(12) United States Patent
Frank et al.

(10) Patent No.: US 9,138,937 B2
(45) Date of Patent: Sep. 22, 2015

(54) DISPOSABLE HYGIENE ARTICLE, SURGICAL COVERING ITEM, OR SURGICAL GARMENT

(75) Inventors: Bernd Frank, Steinheim (DE); Ruediger Kesselmeier, Herbrechtingen (DE); Christian Koch, Bachhagel (DE); Rudolf Groener, Soehnstetten (DE)

(73) Assignee: Paul Hartmann AG, Heidenheim (DE)

( * ) Notice: Subject to any disclaimer, the term of this patent is extended or adjusted under 35 U.S.C. 154(b) by 947 days.

(21) Appl. No.: 13/323,871

(22) Filed: Dec. 13, 2011

(65) Prior Publication Data

US 2012/0143164 A1 Jun. 7, 2012

Related U.S. Application Data

(63) Continuation of application No. 12/310,847, filed as application No. PCT/EP2007/008134 on Sep. 19, 2007, now abandoned.

(30) Foreign Application Priority Data

Sep. 22, 2006 (DE) .......................... 10 2006 046 420

(51) Int. Cl.
*A61F 13/475* (2006.01)
*A61F 13/494* (2006.01)
*B29C 65/00* (2006.01)
(Continued)

(52) U.S. Cl.
CPC ........... *B29C 66/244* (2013.01); *A61F 13/4753* (2013.01); *A61F 13/515* (2013.01); *A61F 13/539* (2013.01); *B29C 65/086* (2013.01); *B29C 66/21* (2013.01); *B29C 66/433* (2013.01); *B29C 66/7294* (2013.01); *B29C 66/81433* (2013.01); *B29C 66/81469* (2013.01); *B29C 66/83511* (2013.01); *B29C 66/72143* (2013.01);
(Continued)

(58) Field of Classification Search
CPC ........... A61F 13/4753; A61F 13/49413; A61F 13/4942; A61F 2013/53925; A61F 2013/53991
USPC ...................... 604/382, 385.28; D24/125–126
See application file for complete search history.

(56) References Cited

U.S. PATENT DOCUMENTS 4,414,045 A * 11/1983 Wang et al. ................... 156/73.2
4,430,148 A * 2/1984 Schaefer ..................... 156/580.2
(Continued)

FOREIGN PATENT DOCUMENTS

JP 2003-265519 9/2003
JP 2006-020976 1/2006
JP 2006-051269 2/2006

*Primary Examiner* — Tan-Uyen (Jackie) T Ho
*Assistant Examiner* — Paula L Craig
(74) *Attorney, Agent, or Firm* — Paul Vincent

(57) ABSTRACT

A disposable hygiene article (2), such as an incontinence diaper or incontinence pad has a composite non-woven fabric (38) that is provided with at least one cuff element (16) and a non-woven fabric or film component (10, 12). The cuff element (14) is attached to the non-woven fabric or film component (10, 12) in at least some areas by means of a joining pattern (36) encompassing discrete ultrasonic welding points (30) in order to form the composite non-woven fabric (38). At least some sections of the joining pattern (36) are curved. The joining pattern has a maximum index (I) of variation of the ultrasonic welding points of 40 percent. An area seized by the welding points has a density within the joining pattern which decreases in rear and front end portions along endwards directed and inwardly curved extensions of the joining pattern.

28 Claims, 8 Drawing Sheets

(51) Int. Cl.
*A61F 13/515* (2006.01)
*A61F 13/539* (2006.01)
*B29C 65/08* (2006.01)
*B29L 31/48* (2006.01)

(52) U.S. Cl.
CPC ... *B29C 66/83411* (2013.01); *B29L 2031/4878* (2013.01)

(56) References Cited

U.S. PATENT DOCUMENTS

| | | | | |
|---|---|---|---|---|
| D276,183 S | * | 10/1984 | Whitehead | D24/125 |
| 4,493,868 A | * | 1/1985 | Meitner | 428/171 |
| 5,494,736 A | * | 2/1996 | Willey et al. | 442/409 |
| 5,624,426 A | * | 4/1997 | Roe et al. | 604/385.28 |
| 5,667,609 A | * | 9/1997 | Liu | 156/73.1 |
| 5,733,411 A | * | 3/1998 | Bett | 156/580.2 |
| 5,810,800 A | * | 9/1998 | Hunter et al. | 604/385.23 |
| D403,763 S | * | 1/1999 | Lynard et al. | D24/125 |
| D403,764 S | * | 1/1999 | Lynard et al. | D24/125 |
| D412,574 S | * | 8/1999 | Trombetta et al. | D24/125 |
| D412,575 S | * | 8/1999 | Trombetta et al. | D24/125 |
| 6,093,665 A | * | 7/2000 | Sayovitz et al. | 442/394 |
| 6,139,941 A | * | 10/2000 | Jankevics et al. | 428/195.1 |
| D445,498 S | * | 7/2001 | Renz et al. | D24/125 |
| D448,476 S | * | 9/2001 | Page et al. | D24/124 |
| 6,547,903 B1 | * | 4/2003 | McNichols et al. | 156/64 |
| 6,572,599 B2 | * | 6/2003 | Drevik | 604/385.27 |
| 6,620,490 B1 | * | 9/2003 | Malchow et al. | 428/196 |
| 6,652,500 B2 | * | 11/2003 | Daniels et al. | 604/385.01 |
| 6,713,159 B1 | * | 3/2004 | Blenke et al. | 428/195.1 |
| 6,717,028 B1 | * | 4/2004 | Oberstadt | 604/365 |
| 7,674,949 B2 | * | 3/2010 | Wahlstrom et al. | 604/380 |
| 8,575,419 B2 | * | 11/2013 | Di Virgilio et al. | 604/380 |
| 2002/0048652 A1 | * | 4/2002 | Malchow et al. | 428/194 |
| 2002/0062901 A1 | * | 5/2002 | Couillard et al. | 156/73.1 |
| 2003/0041953 A1 | * | 3/2003 | Farell et al. | 156/181 |
| 2004/0176734 A1 | * | 9/2004 | Rasmussen et al. | 604/380 |
| 2006/0149202 A1 | * | 7/2006 | Cardin et al. | 604/385.04 |
| 2006/0149209 A1 | * | 7/2006 | Malchow et al. | 604/389 |
| 2007/0066948 A1 | * | 3/2007 | Erdman | 604/380 |
| 2009/0292266 A1 | * | 11/2009 | Back | 604/365 |
| 2010/0059067 A1 | * | 3/2010 | Frank et al. | 128/849 |

* cited by examiner

DISPOSABLE HYGIENE ARTICLE, SURGICAL COVERING ITEM, OR SURGICAL GARMENT

This application a continuation of Ser. No. 12/310,847 filed Mar. 10, 2009, now abandoned as the national stage of PCT/EP2007/008134 filed on Sep. 19, 2007 and also claims Paris Convention priority of DE 10 2006 046 420.6 filed Sep. 22, 2006, the entire disclosures of which are hereby incorporated by reference.

BACKGROUND OF THE INVENTION

The invention relates to a disposable hygiene article or surgical covering item, or surgical garment for single use, such as an incontinence diaper, incontinence pad, surgical drape, or surgical coat, comprising a composite nonwoven fabric, that is provided with at least one nonwoven fabric component and another nonwoven fabric or film component. The first nonwoven fabric component is attached to the other nonwoven fabric or film component in at least some areas by means of a joining pattern encompassing discrete ultrasonic welding points in order to form the composite nonwoven fabric. The joining pattern extends in a longitudinal direction and a transverse direction that runs perpendicular thereto, the distance in the longitudinal direction being longer than the distance in the transverse direction. At least some sections of the joining pattern are curved.

For example, on hygiene articles, in particular, incontinence products, such as incontinence diapers, lateral barriers standing toward the user during use, called cuff elements, are provided that comprise a nonwoven fabric component and are attached in the longitudinal direction of the product to another nonwoven fabric or film component of the hygiene article by means of ultrasonic welding or bonding. In the field of the hygiene articles addressed here, the joining of nonwoven fabric and/or film components by means of ultrasonic welding devices is generally known. For example, a joining pattern comprising discrete ultrasonic welding points can be implemented in a continuous, that is, never-ending production machine for nonwoven articles of the type stated above by using a contour roller rolling in the machine direction and an anvil made to vibrate in the ultrasonic range, which is termed a sonotrode. The contour roller and sonotrode form a gap between them through which the weldable components to be joined are fed during the continuous production process. The nonwoven fabric or film components are then welded by transfer of the vibration energy on the raised areas of the contour roller. The strength of the weld can be adjusted by varying the distance between the sonotrode and the contour roller and by controlling the vibration of the sonotrode.

The applicant has ascertained that, in particular, on fast-operating production machines, it is extremely difficult to achieve a uniformly secure weld without damaging the components if the area of the weld varies greatly in the machine direction, because this necessitates very frequent variation in control of the welding device or its sonotrode. It is extremely difficult to almost impossible to achieve a stable operating condition. If, on the other hand, the area of a joining pattern varies little or not at all in the machine direction, for example, if it does not vary in the circumferential direction of the contour roller and, for example, comprises concentric embossing lines or embossing points on the contour roller, the problem described above does not occur because the welded area does not change so rapidly in the machine direction. If, on the other hand, the joining pattern is oblique with respect to the machine direction or comprises oblique sections, the proportion of the welded area in the machine direction will vary greatly and the problems described above will occur. If, for example, on one product, the joining pattern comprises arc-shaped areas with tight curvature with respect to the machine direction, achieving process reliability in the welding of nonwoven fabric components poses a problem. If this problem is not solved, unwelded points or damage to the nonwoven fabric or film components due to overwelding will occur. In either case, correct functioning of the article being produced is jeopardized. Extremely short control cycles in operating the ultrasonic welding device can also result in the device overshooting and frequently causing direct contact between the contour roller and the sonotrode. This results in damage to the device, considerably reducing its service life. The sonotrode and contour roller then require frequent replacement due to the high wear caused by direct contact between the two machine components.

The object of this invention is to provide a hygiene article or a surgical covering item or surgical garment of the type described above with which the problems described above do not occur, while nevertheless permitting production of a joining pattern of discrete ultrasonic welding points that varies in the machine direction. For example, it must be possible to fix a standing cuff element according to a joining pattern that oscillates in the form of arcs with respect to the machine direction or generally to join weldable nonwoven fabric or film components of the article stated above fed in as flat material without being limited to a joint that is precisely straight in the machine direction. In particular, damage to components being welded together during the welding process and partially deficient welding of the components must be precluded. Similarly, damage to the ultrasonic welding device must be avoided and a long service life ensured in conjunction with fast-operating production machines.

SUMMARY OF THE INVENTION

This object is inventively achieved with a hygiene article, incontinence diaper or incontinence pad, the article having a longitudinal direction and a transverse direction perpendicular to the longitudinal direction as well as a central axis extending in the longitudinal direction. The inventive article comprises a nonwoven fabric or film component and at least one cuff element on a left and right side of the hygiene article forming a left and right upstanding leakage barrier and extending substantially in the longitudinal direction of the article. Discrete ultrasonic welding points are disposed in a joining pattern to attach the cuff element to the nonwoven fabric or film component. An extension of the joining pattern in the longitudinal direction exceeds an extension of the joining pattern in the transverse direction, the joining pattern having a central portion travelling substantially in the longitudinal direction of the article as well as rear and front end portions. The rear and front end portions of the joining pattern curve inwardly towards the central axis of the article along an endwards directed extension of the joining pattern. An index of variation of the joining pattern is no more than 40% and an area seized by the ultrasonic welding points in the joining pattern has a density within the joining pattern which decreases in the rear and front end portions along the endwards directed and inwardly curved extension of the joining pattern. The solution to the object of the invention is therefore to design the joining pattern of the ultrasonic welding points in such a way that the area seized by the welding in the machine direction does not vary so much that the problems described above occur. For example, this can be achieved by variation and appropriate disposition of the number of ultrasonic welding points per unit area, that is, e.g. by selecting the distance between the ultrasonic welding points and/or by varying the respective area of the ultrasonic welding points.

The index of variation of the ultrasonic welding points is calculated as follows: The article in accordance with the invention is considered divided into 5-mm wide longitudinal sections in the first direction. These longitudinal sections therefore extend over 5 mm in the longitudinal direction, which is also the machine direction, and perpendicular thereto in the transverse direction, which is the transverse direction on the product. Each of these sections extending 5 mm in the longitudinal direction encompasses a number of ultrasonic welding points, each of which constitutes a welded proportion of the area. It is possible to calculate the welded area $A_i$ of each 5-mm section (sum of the areas of the individual ultrasonic welding points in a 5-mm section). It is also possible to calculate a mean value $\overline{A}$ of the area $A_i$ seized by the ultrasonic welding points of each section. For example, it is possible to divide an 820-mm long article into 164 such 5-mm sections in the longitudinal direction. For each section, it is possible to calculate the welded area $A_i$ and from these 164 $A_i$ values, it is then possible to calculate the arithmetic mean $\overline{A}$ of the welded area of the 5-mm sections. A value s can be calculated from these according to the following formula:

$$s = \sqrt{\frac{1}{N-1} \sum_{i=1}^{N} (A_i - \overline{A})^2}$$

Thus the error sum of squares of $A_i$ of the individual 5-mm sections is calculated from the mean value $\overline{A}$ of the welded surfaces of the 5-mm sections and divided by (N−I) and the square root is taken of the result. Based on this, the index I (in %) of variation of the ultrasonic welding points is defined as follows:

$$I = \frac{s}{\overline{A}} \times 100 [\%]$$

It has been shown that the range of the index of variation of the ultrasonic welding points of no more than 40% is suitable, in particular, for the machine velocities relevant here of 100 m/min to 1000 m/min, in particular, of 150 m/min to 700 m/min, to ensure process reliability of the ultrasonic weld joint between nonwoven fabric components and/or film components of the articles in question here. It has proven especially advantageous if the index of variation of the ultrasonic welding points is no more than 35%, in particular, no more than 30% and further, in particular, no more than 25%.

This invention proves especially advantageous on an article in which the composite nonwoven fabric comprises on both sides at least one cuff element standing at least in sections, forming a leakage barrier, and essentially extending in the longitudinal direction. As mentioned above, a cuff element is a lateral barrier formed from a flat material that is raised from the substrate mostly due to elastification, in particular, toward the body of the user and thus provides a leakage barrier, chiefly at the sides of the article. In the case of an inventive article, this cuff element is joined to further (chassis) nonwoven fabric or film components of the article by an inventively constituted joining pattern of ultrasonic welding points.

In particular, if the article according to the claims is a hygiene article for single use, it proves advantageous if the article comprises a topsheet that is permeable at least in some areas, a backsheet that is impermeable at least in some areas, and a storage core that absorbs body fluids and is disposed between the two. In such a case, it can be advantageous for the nonwoven fabric or film component to be the topsheet or the backsheet, so that the cuff element is attached to the topsheet or backsheet by the inventive joining pattern of ultrasonic welding points.

To join a cuff element to further components of the article by means of ultrasonic welding, it proves advantageous if the joining pattern comprises a first partial joining pattern that, at least in areas, constitutes a cuff base, that is, an area along which the cuff element is attached to the further nonwoven fabric component or film component. When the article is put to its intended use, this then constitutes a fold line along which the cuff element is raised away from a base plane.

In a further embodiment of this inventive concept, the cuff base constituted in some areas by the first partial joining pattern can additionally be constituted or limited in some areas by a second partial joining pattern that is substantially straight and, in particular, largely extends parallel to the longitudinal direction. Here and hereafter a partial joining pattern is referred to as substantially straight when, over a length of 200 mm in the longitudinal direction, an extension in the transverse direction of no more than 6 mm can be ascertained.

In yet a further embodiment, the cuff base is constituted at least in sections by the first partial joining pattern, the second partial joining pattern and a third curved partial joining pattern. In the first direction, the second partial joining pattern is disposed preferably between the first and the third partial joining pattern. The result is therefore a cuff base that, in a front area and in a rear area of the article, extends transverse to the longitudinal direction, in particular, curved in the shape of an arc with respect to the longitudinal direction and, in the intermediate area, is substantially straight and, in particular, parallel to the longitudinal direction. Such a configuration proves especially advantageous, particularly for hygiene articles for single use, such as incontinence diapers, incontinence pads. The invention makes it possible to dispose the cuff elements relatively far toward the outside in the transverse direction in a front and rear region of the article and then to have them curve inwardly toward the crotch area. In the crotch area, the cuff elements or the cuff base or cuff base lines then advantageously extend largely parallel and have a smaller distance between them in the transverse direction than in the front and rear areas. With this invention, it becomes possible to establish a stable connection between the cuff element and chassis materials of a hygiene article that meets the desired requirements for configuration of the article and is nevertheless producible with process reliability by complying with the inventive design of the joining pattern.

In a further embodiment of the invention, it proves advantageous if, in an inventive article, the joining pattern in the longitudinal direction is considered virtually in three sections of equal length, that is, is divisible into a start section, an adjoining center section, and an end section adjoining the center section and the index of variation of the area of the start section and/or of the end sections of the joining pattern is no more than 40%, in particular, no more than 35%, further, in particular, no more than 30%, further, in particular, no more than 25%. According to this further embodiment of the invention, the inventively imposed condition is not only fulfilled over the entire claimed article, considering all 5-mm sections containing ultrasonic welding points, but also for the corresponding 5-mm sections of the start section overlapping by one third and the end section overlapping by one third.

As already stated, the inventive design of the joining pattern of the ultrasonic welding points can be achieved by various measures. In particular, it can prove advantageous if the distance between the discrete ultrasonic welding points is smaller in a first area than in a second area.

In particular, it proves useful if the distance between individual (discrete) ultrasonic welding points in a first area is 0.1 to 2.5 mm, in particular, 0.2 to 1.5 mm, and further, in particular, 0.2 to 1.0 mm and, in a second area, is 2 to 20 mm, in particular, 3 to 15 mm, further, in particular, 4 to 10 mm.

It is also possible for the density per unit area of the ultrasonic welding points (number of points per unit area) to be greater in a first area than in a second area.

The first area is a partial area of the joining pattern; it can constitute, in particular, one partial area of the first and/or second and/or third partial joining pattern of the cuff base.

According to a further embodiment of the invention, the first and/or third partial joining pattern comprises a set of at least two, in particular, at least three curves, further, in particular, at least four, further, in particular, at least five curves. Preferably at least two of the curves of a set should be separated by a small maximum distance of 2 to 20 mm, in particular, 2 to 15 mm and further, in particular, 3 to 10 mm. Furthermore, it proves advantageous if at least two of the curves of a set are separated by a greater maximum distance of 10 to 70 mm, in particular, 15 to 60 mm and further, in particular, 20 to 50 mm. For example, this is possible and advantageous if the set consists of three curves and the maximum distance of the first outer curve from the center curve has the previously stated low value and the maximum distance of the second outer curve from the center curve is a greater distance. Of course, in the case of a set of more than three curves, at least two curves of a set can have a different maximum distance between them.

Moreover, it proves advantageous if one or more of the curves has a radius of at least 60 mm, in particular, at least 70 mm, further, in particular, 80 mm, further, in particular, at least 90 mm, further, in particular, at least 100 mm and further, in particular, no more than 150 mm. The curves can also have a variable distance between them.

The curves are advantageously not a weld line that is continuous over its extension but a series of consecutive ultrasonic welding points that is then largely linear and thus forms the curve. By varying the distance between the ultrasonic welding points and/or by changing the distance between the curves it is possible to vary the proportion of the area of the weld points in each 5-mm section, so that, overall, the claimed index range is complied with.

It proves advantageous if the joining pattern has first discrete ultrasonic welding points with an area of 0.3 to 4 $mm^2$, in particular, 0.3 to 3 $mm^2$, further, in particular, 0.3 to 2 $mm^2$, further, in particular, 0.5 to 1.1 $mm^2$ and further, in particular, 0.7 to 0.9 $mm^2$.

As already stated, it can be advantageous if the joining pattern encompasses first and second discrete ultrasonic welding points and the area of the first discrete ultrasonic welding points is smaller than that of the second discrete ultrasonic welding points.

The shape of the area of the ultrasonic welding points is relatively uncritical; they can be circular or oval or triangular or polygonal or sickle-shaped or dot-and-dashed or star-shaped or linear.

For example, in the production of hygiene articles, it can prove advantageous if the sum ($A_i$) of the areas of the ultrasonic welding points of a 5-mm long section of the joining pattern in the longitudinal direction is on average 2 to 25 $mm^2$, in particular, 3 to 18 $mm^2$, in particular, 4 to 12 $mm^2$ and further, in particular, 6 to 10 $mm^2$. In the case of a hygiene article with cuff elements on both sides, these are preferably the values that apply to the joining pattern of one of the cuff elements.

Furthermore, it proves advantageous if the sum ($A_i$) of the areas of the ultrasonic welding points of one, in particular, each 5-mm long section of the joining pattern in the longitudinal direction is no more than 30 $mm^2$, in particular, no more than 23 $mm^2$, further, in particular, no more than 18 $mm^2$, further, in particular, no more than 16 $mm^2$, further, in particular, no more than 15 $mm^2$.

In the production of an inventive article, it proves advantageous if, in the design of the joining pattern of the ultrasonic welding points, the deviation of the sum ($A_i$) of the areas of the ultrasonic welding points of each 5-mm long section of the joining pattern in the longitudinal direction from the sum ($A_i$) of the areas of the ultrasonic welding points of a directly adjacent 5-mm long section of the joining pattern is less than 70%, in particular, less than 60%, in particular, less than 50%, further, in particular, less than 40%. This means that the entire welded area ($A_i$) of two adjacently disposed 5-mm sections must differ by no more than the above-mentioned ranges. In this case, this deviation of two adjacent 5-mm long sections refers to the sum $A_i$ of the areas of the ultrasonic welding points of the section whose sum $A_i$ of the areas of the ultrasonic welding points has the higher value.

Furthermore, it proves advantageous with respect to consistent product quality if the deviation of the sum of the areas of the ultrasonic welding points of at least 50%, in particular, of at least 60%, further, in particular, of at least 70% and further, in particular, of at least 80%, and, very especially, of at least 90% of the 5-mm long sections of the joining pattern from the sum ($A_i$) of the areas of the ultrasonic welding points of a directly adjacent 5-mm long section of the joining pattern is less than 40%, in particular, less than 30%, in particular, less than 25%.

The invention also relates to a method for the production of a hygiene article or surgical covering item, or surgical garment of the inventive type with the characteristics claimed.

Furthermore, it proves advantageous if the claimed article is constituted such that the joining pattern extends 300 to 2000 mm, in particular, 350 to 1500 mm, in particular, 400 to 1200 mm, further, in particular, 450 to 1100 mm and further, in particular, 500 to 1000 mm in a longitudinal direction and running perpendicular thereto preferably 10 to 1200 mm, in particular, 15 to 1000 mm, in particular, 20 to 500 mm, further, in particular, 30 to 200 mm and further, in particular, 40 to 150 mm and further, in particular, 50 to 130 mm in a transverse direction.

Further characteristics, details, and advantages of the invention can be seen from the appended patent claims and from the drawings and the following description of the invention using explanatory examples. The drawings show:

DESCRIPTION OF THE PREFERRED EMBODIMENT

Figure 1:
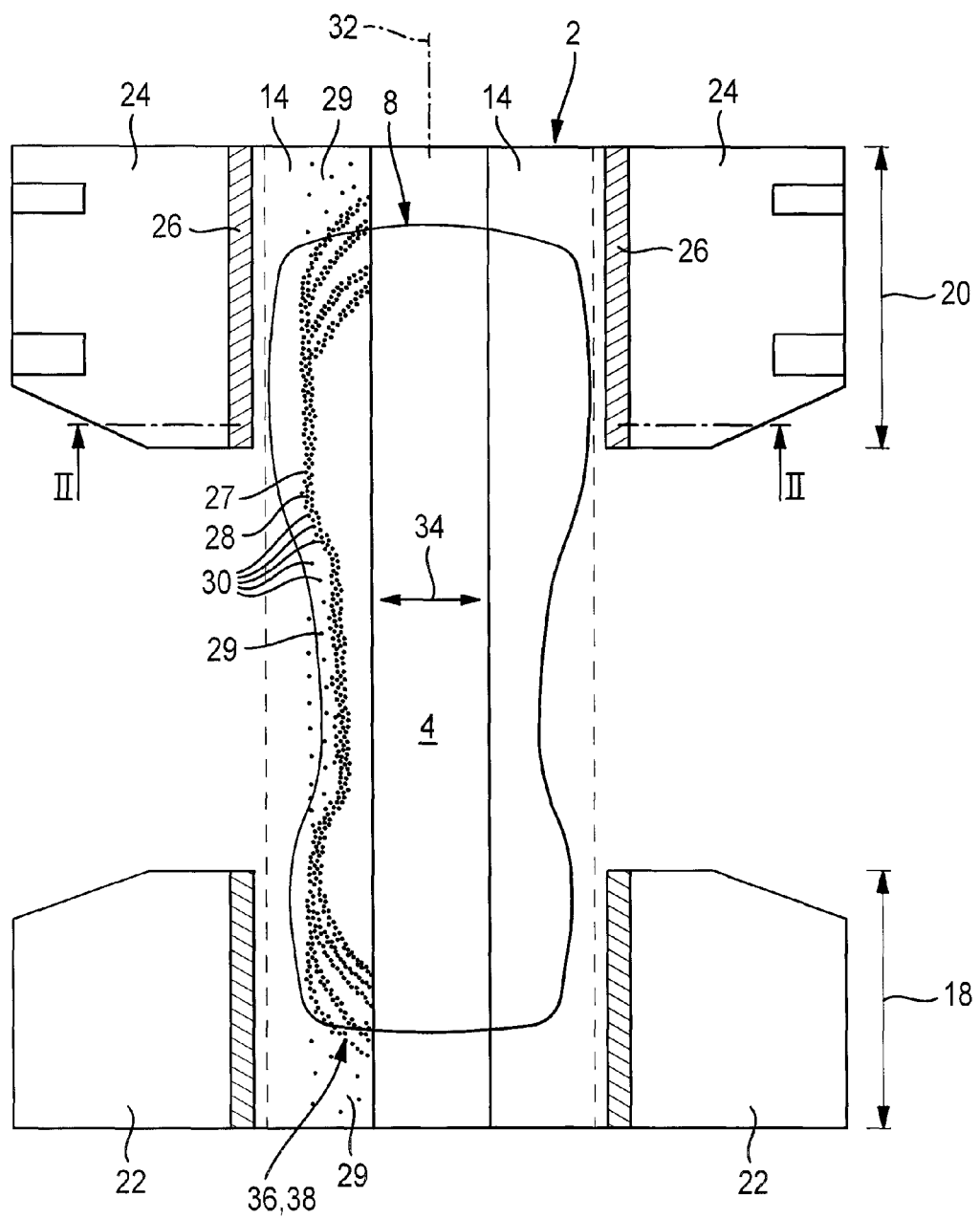
FIG. 1 a top view of a hygiene article in the form of an incontinence diaper in the unfolded condition.
Figure 2:
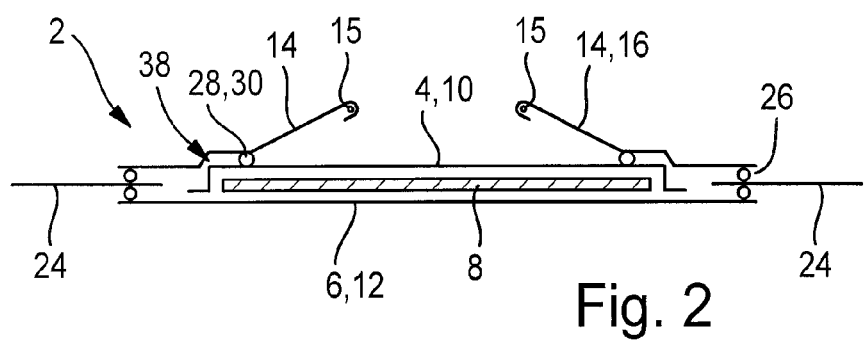
FIG. 2 a sectional view with intersection plane II-II in FIG. 3.

FIG. 1 shows a hygiene article numbered in its entirety with the reference symbol 2 in the form of an incontinence diaper for single use. FIG. 2 depicts a schematic sectional view with intersection plane II-II in FIG. 1. Hygiene article 2 comprises a topsheet 4 and an impermeable backsheet 6 and an interposed absorption body 8. The topsheet 4 is a permeable nonwoven fabric component, in particular, a card or spunbonded nonwoven, preferably with a mass per unit area of 8-30 g/m², in particular, 12 to 25 g/m², in particular, 14 to 22 g/m² and the backsheet 6 is an impermeable film component or a composite nonwoven/film material 12. Moreover, as is best seen in FIG. 2, the hygiene article comprises lateral cuff elements 14 with thread-like elastification means 15 disposed on their distal edge, fixed on them in the pretensioned condition preferably by hot melt adhesive, which form a lateral leakage barrier. These cuff elements 14 also preferably comprise a nonwoven fabric component 16, in particular, a hydrophobic spunbonded nonwoven or a spunbond-meltblown (SM) or a spunbond-meltblown-spunbond (SMS) nonwoven laminate with a mass per unit area of 8 to 30 g/m², in particular, 12 to 20 g/m², in particular, 13 to 18 g/m².

Laterally extending side flaps 22 and 24 are provided in a respective front area 18 and in a respective back area 20. The side flaps 22, 24 extend between topsheet 4 and backsheet 6 and are fixed there by welding or gluing. A weld or glue line is indicated with reference symbol 26.

Moreover, the cuff elements 14 of both sides are joined in a first area 27 along a so-called cuff base 28 and in a second area 29 with the nonwoven fabric component 10 of the topsheet 4 by discrete ultrasonic welding points 30 forming a joining pattern. The discrete ultrasonic welding points 30 have a maximum distance between them of 0.1 mm to 2.5 mm in a first area 27 and a maximum distance between them of 4.0 mm to 10.0 mm in a second area 29 and have an area of 0.7 to 0.9 mm² in each case. The extent of the cuff base 28 is best visible in FIG. 1. For better clarity only, FIG. 1 does not show the second joining pattern that fixes the right cuff element to the topsheet 4. The second joining pattern that is not shown is the mirror image of the first.

It would be possible and advantageous, in an embodiment not shown here, to fix the cuff base 14 directly to the backsheet 6 by means of the joining pattern. This would be advantageous, in particular, if the cuff base 14 were outside the absorption body contour and outside the transverse extent of the topsheet 4.

Hygiene article 2 furthermore has a first direction 32 that constitutes the longitudinal direction of the hygiene article and matches the machine direction during production of the hygiene article. In continuous production, the topsheet 4, backsheet 6, side flaps 24, and cuff elements 14 constituting the corresponding webs of flat material therefore extend in this first direction 32. The cuff base 28 or the series of ultrasonic welding points 30 also largely extends along this first direction 32. However, as can be seen in FIG. 1, the cuff base 28 is, at least in areas, not straight and parallel to the first direction 32, but extends in the shape of a curve or arc and therefore also has a component in a second direction 34 that is perpendicular to the first direction (transverse direction of the hygiene article). The joining pattern 36 that is at least partially formed by the ultrasonic welding points 30 will be described in detail below. The nonwoven fabric components and/or film components that are permanently joined to each other while the article is being put to its intended use also constitute a composite nonwoven fabric 38.

Figure 3:
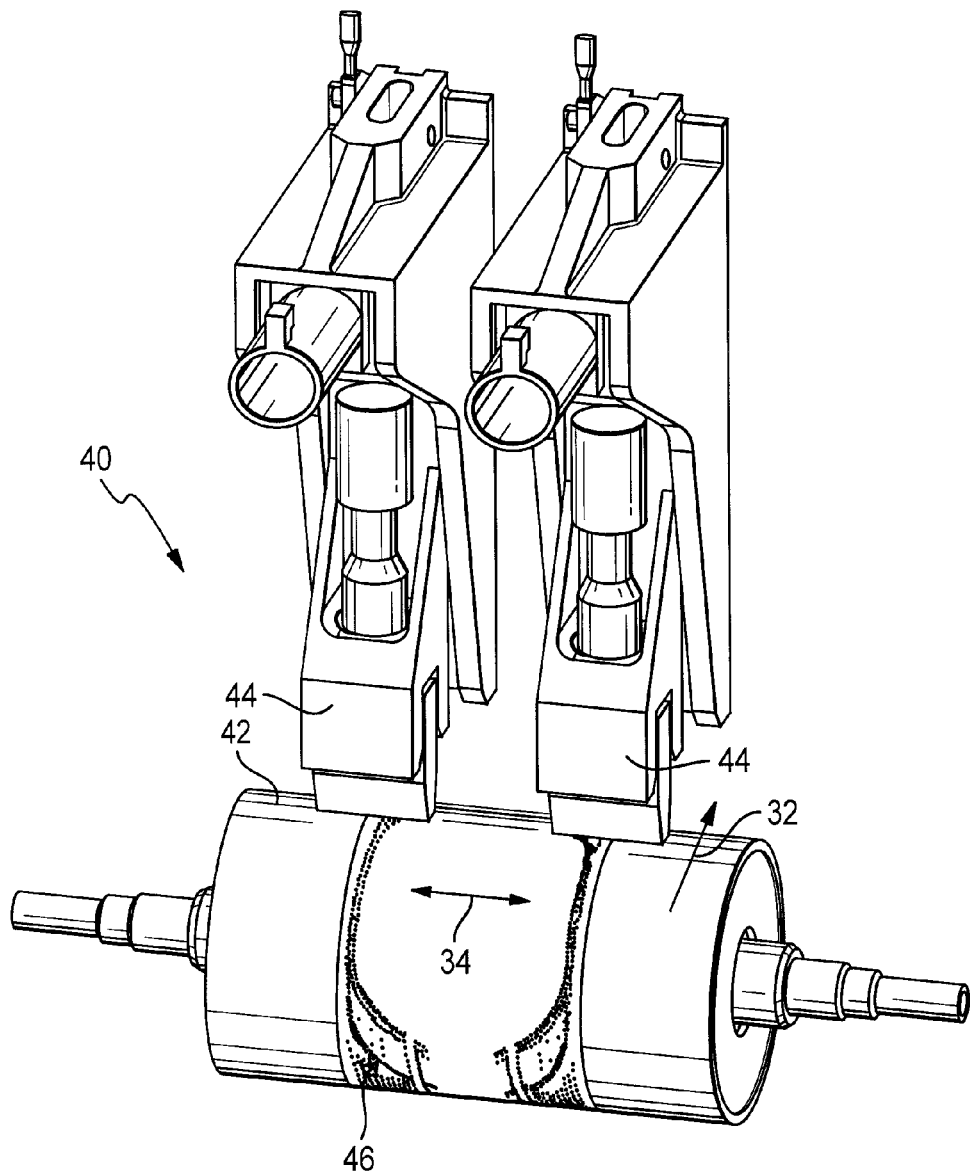
FIGS. 3, 4 a partially perspective view of an ultrasonic welding device for production of inventive articles in a continuous production process using continuously fed flat material.
Figure 4:
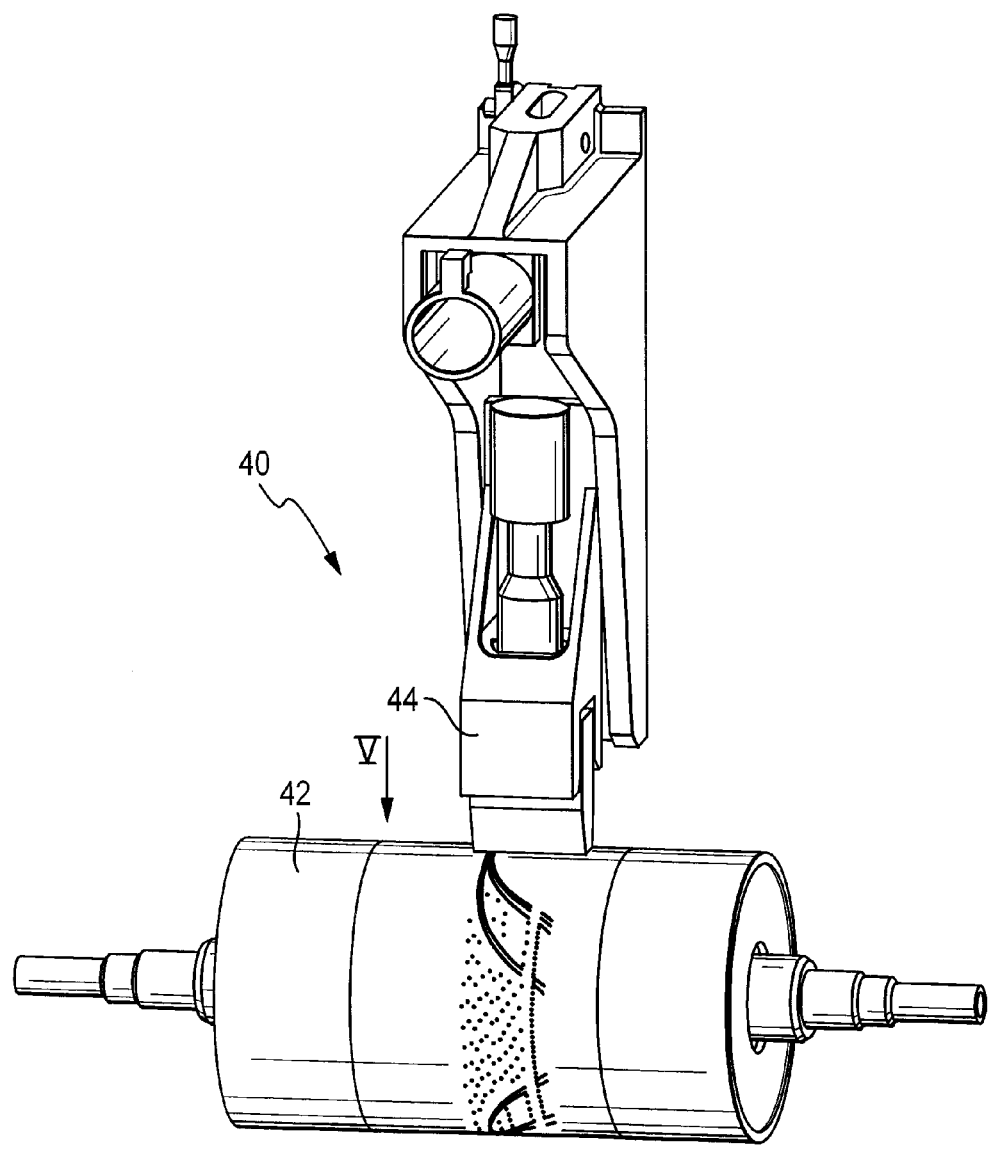

The schematic representation of an ultrasonic welding device designated in its entirety with reference sign 40 in FIGS. 3, 4 illustrates a contour roller 42 that rolls in the machine direction or first direction 32 and a sonotrode 44 that can be excited in the ultrasonic range. The ultrasonic welding device 40 can be integrated into a fast-operating machine for producing modern hygiene articles. FIG. 3 depicts an ultrasonic welding device with two sonotrodes 44 for producing the welded joint between two cuff elements on both sides, while the device according to FIG. 4 only shows one sonotrode 44 and is only intended for production of the ultrasonic welded joint with one cuff element. The corresponding further contour roller and sonotrode for the other half could be disposed before, after, or parallel with the first. It is also possible, in the case of the embodiment according to FIG. 3, to have a single continuous sonotrode in the second direction 34 instead of two parallel sonotrodes.

During production of the hygiene articles shown in FIGS. 1 and 2, for example, a cuff element 14 and the topsheet 4 in a configuration with one on top of the other would be introduced into the gap of the ultrasonic welding device constituted by the sonotrode and contour roller according to FIG. 3 to join these components to form the composite nonwoven fabric and to place it on the absorption body 8.

Figure 5:
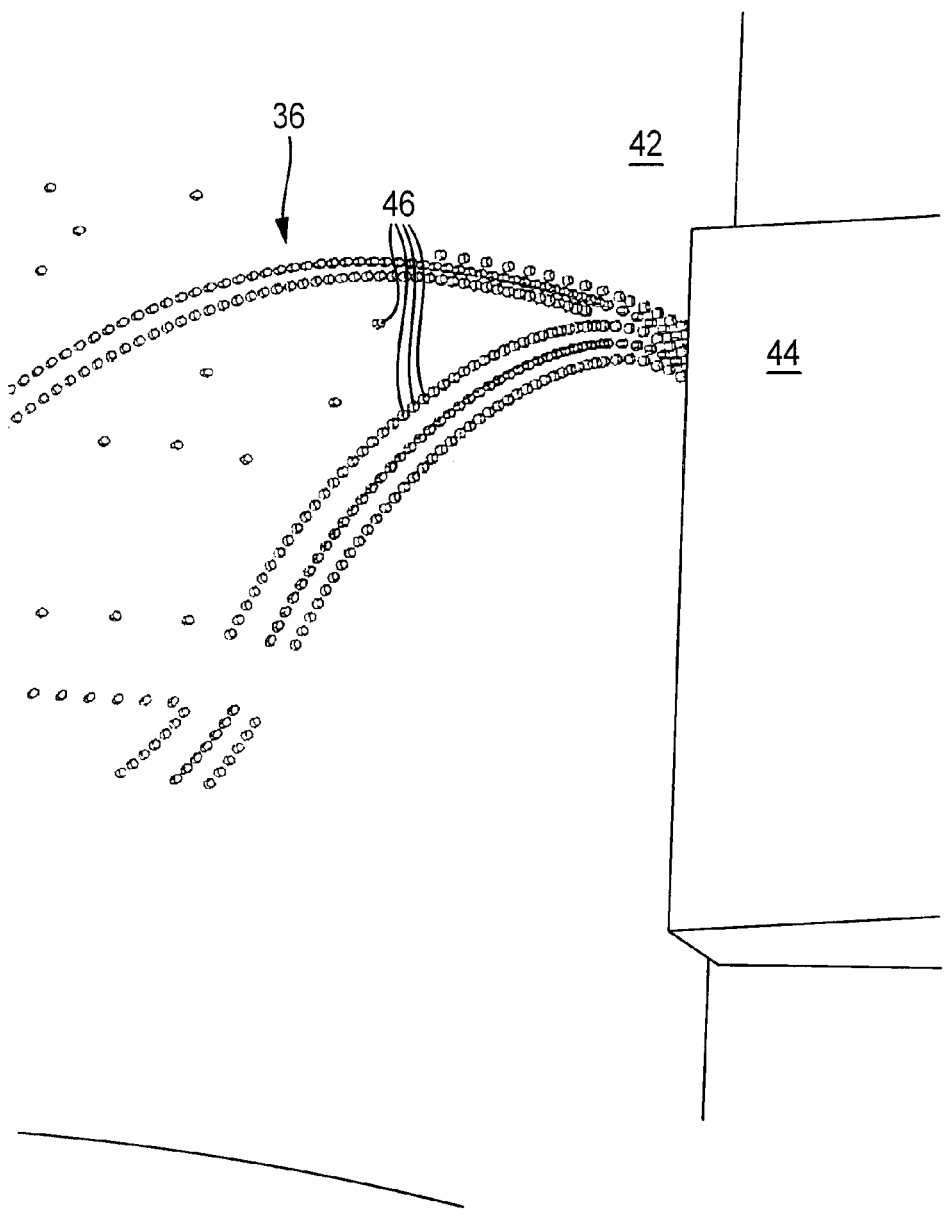
FIG. 5 an enlarged detailed view of a joining pattern from FIGS. 5, 6 (viewed as a top view according to the Arrow V onto the device according to FIG. 4.

On the circumference of the contour roller 42, numerous protrusions 46 can be seen that are disposed and constituted according to the joining pattern 36 to be produced. FIG. 5 shows a top view onto the surface of the contour roller 42 viewed in the direction of arrow V in FIG. 4. The figure shows the protrusions 46 on the contour roller 42 and the corresponding identical joining pattern 36 produced by them as the roller turns on the flat material web being fed through. A linear or serial configuration of protrusions 46 that constitute ultrasonic welding points 30 of the subsequent cuff base 28 can be seen. Moreover, it can be seen that the distance between the protrusions 46 and the number of protrusions 46 per unit area on the roller surface 42 vary, so that the conditions described in detail below for the relevant joining pattern 36 are met.

Figure 6:
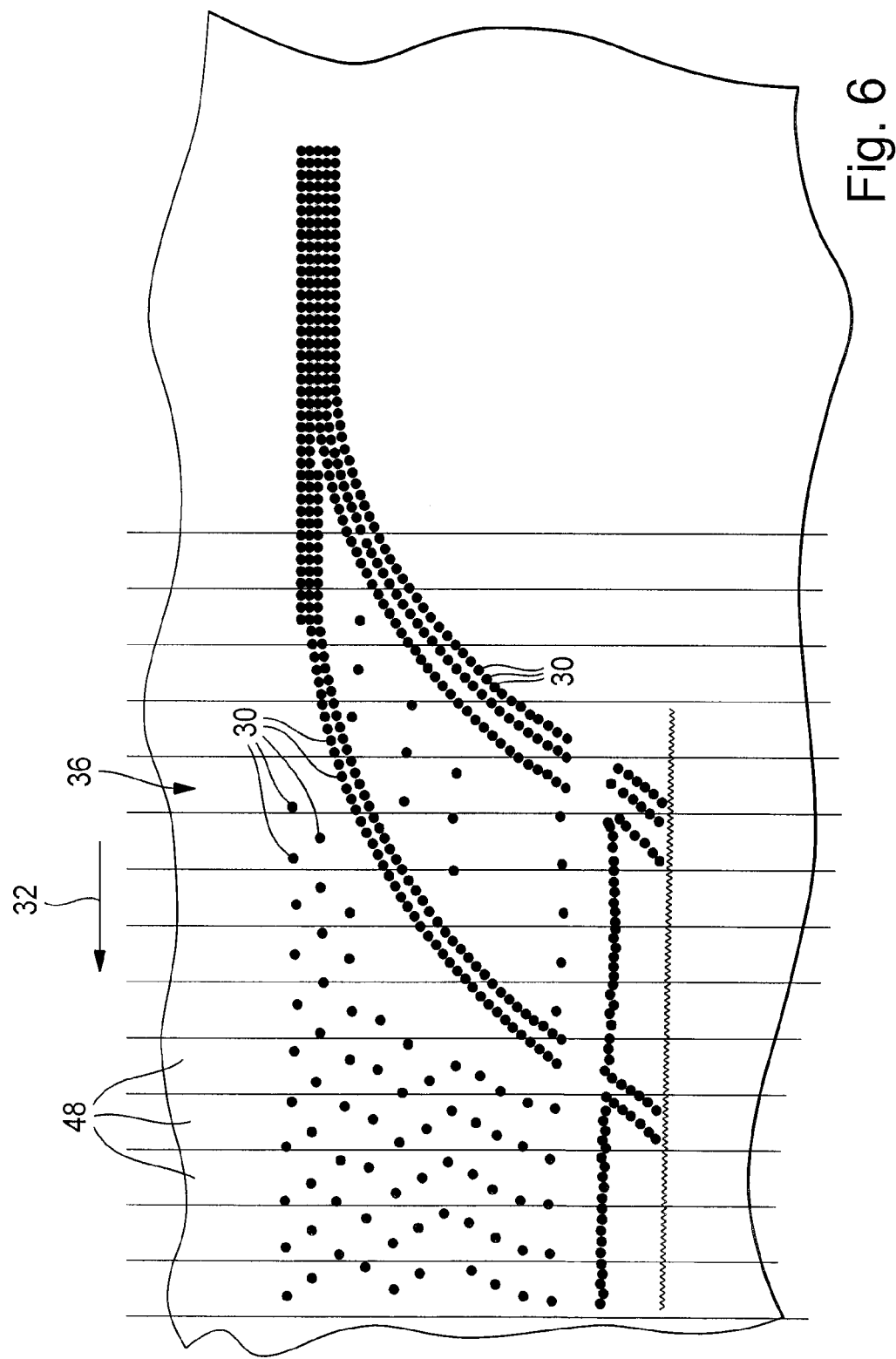
FIG. 6 a top view of an inventively constituted joining pattern to illustrate the conceptual division into 5-mm sections.

FIG. 6 shows a schematic top view of a joining pattern to illustrate the conceptual division of the joining pattern into 5-mm wide sections 48 in the longitudinal direction 32. The sections 48 are therefore contiguous in the first direction 32. Within each 5-mm section 48, a number of ultrasonic welding points 30 are provided that form for each 5-mm section 48 a proportion $A_i$ of embossed or welded area. If N such 5-mm sections 48 are provided that are conceptually disposed in the first direction 32 from the beginning to the end of the ultrasonic joining pattern 36, a mean value $\overline{A}$ can be calculated as follows:

$$\overline{A} = \frac{\sum A_i}{N}$$

It is also possible to calculate a value s from the error sum of squares of the individual $A_i$ values from this mean value $\overline{A}$ according to the following formula:

$$s = \sqrt{\frac{1}{N-1}\sum_{i=1}^{N}(A_i - \overline{A})^2}$$

From this, it is possible to derive an index I of variation of the ultrasonic welding points in the first direction 32 for the entire joining pattern 36 or the conceptual division into N 5-mm sections 48 as follows:

$$I = \frac{s}{\overline{A}} \times 100[\%]$$

It was inventively determined that this index of variation of the ultrasonic welding points 30 should be no more than 40% in the first direction 32.

Based on FIGS. 7 and 8, two different joining patterns of discrete ultrasonic welding points are examined below. As can be seen, it is a joining pattern for fixing cuff elements 14 shown in FIGS. 1 and 2, that is, fixing the nonwoven fabric component 16 of these cuff elements 14 to a further nonwoven fabric or film component 10 of a hygiene article. The joining pattern of one of the two cuff elements 14 of the hygiene article was considered.

Figure 7:
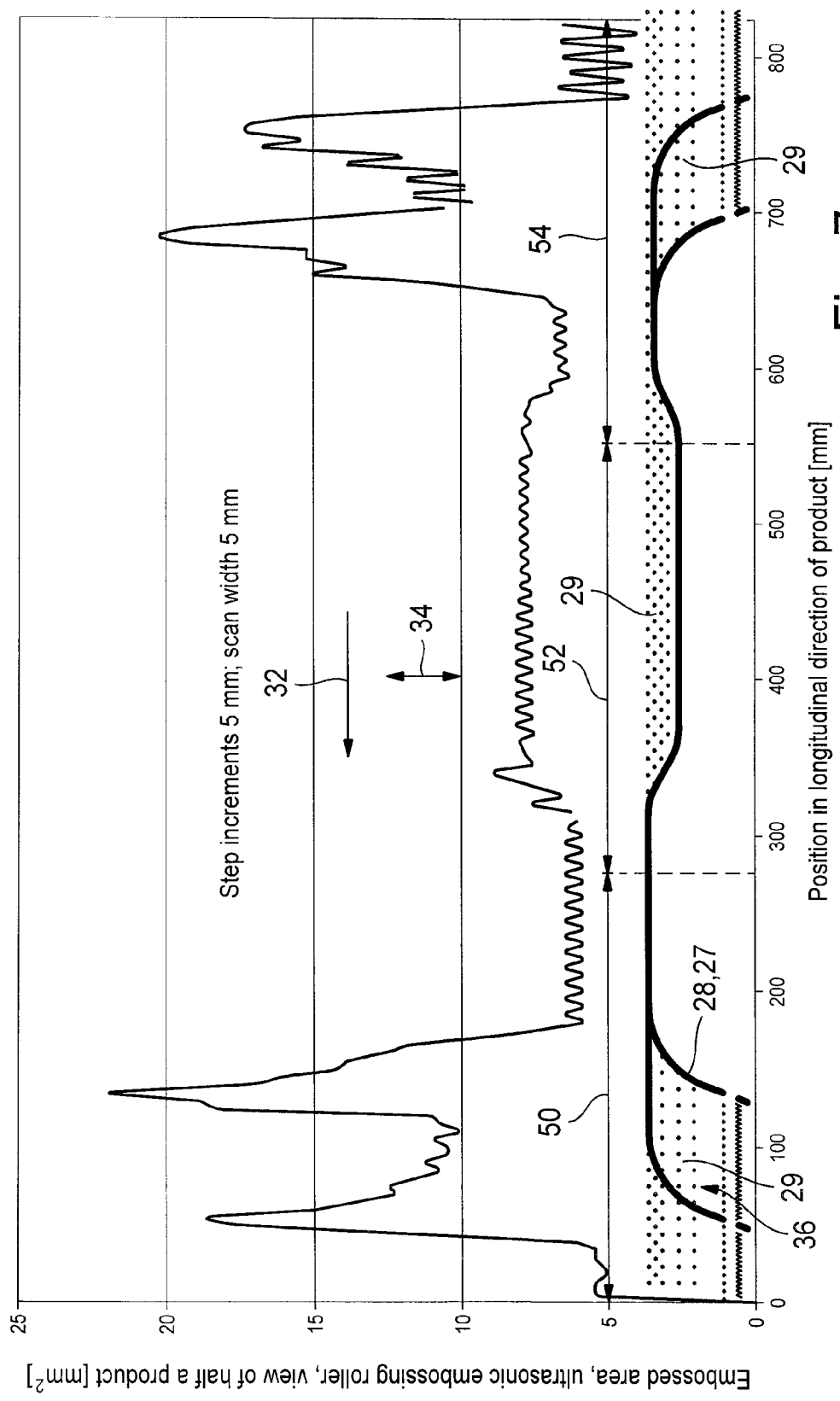
FIG. 7 a diagram in which the area proportion of the ultrasonic welding points of each 5-mm section is entered and the underlying joining pattern is indicated (not comprised in the scope of protection of the invention)

The lower part of FIG. 7 shows along the abscissa the form of the joining pattern under consideration of ultrasonic welding points that have a small distance between them in a first area 27 and a larger distance between them in a second area 29. The extent of the joining pattern in the first direction (machine direction) is 820 mm, resulting in 164 5-mm sections. Above the said joining pattern, FIG. 7 shows those welded proportions of the area within each relevant 5-mm section, which are connected to form a curve. There are therefore 164 area proportions $A_i$, one for each 5-mm section. Due to the relatively small radius of curvature of the cuff bases 28 having a high raster density of the ultrasonic welding points, a very high variation of the area proportions can be seen in the first direction 32. However, this results in the problems described above. The curve shown for the area proportions $A_i$ results in a mean value of 9.01 mm² over all N=164 5-mm sections. This results in a value s of 3.85 and in an index I of 42.7%.

If the joining pattern 36 is divided into a start section 50, a center section 52, and an end section 54 that each extend over a third of the extent of the joining pattern 36 in the longitudinal direction, the following values are obtained for these sections 50, 52, 54 when the N/3 5-mm sections contained in them are each evaluated in isolation:

Start section: $\overline{A}$=9.55, s=4.66, I=48.8%
Center section 52: $\overline{A}$=7.62, s=0.71, I=9.3%
End section 54: $\overline{A}$=9.90, s=4.49, I=45.3%.

Due to this value of the index I of variation of the ultrasonic welding points, a hygiene article with the joining pattern 36 shown in FIG. 7 would not be in accordance with the invention.

Figure 8:
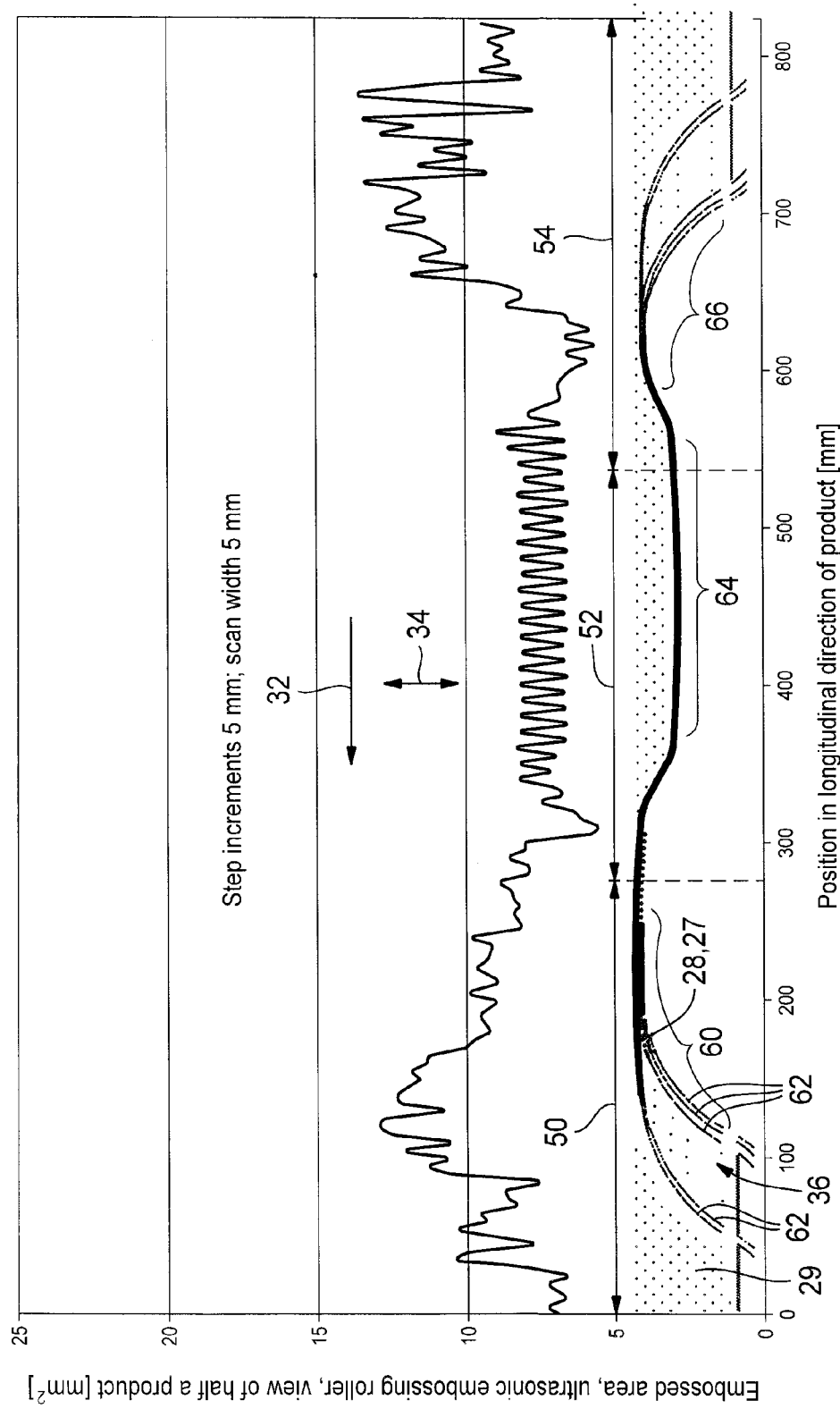
FIG. 8 a corresponding diagram with an inventively constituted joining pattern structure.

An inventive joining pattern 36 is shown in FIG. 8. The following values are obtained when the N/3 5-mm sections contained in sections 50, 52, 54 are each evaluated in isolation:

Start section: $\overline{A}$=9.56, s=1.67, I=17.5%
Center section 52: $\overline{A}$=7.34, s=0.91, I=12.4%
End section 54: $\overline{A}$=9.25, s=2.33, I=25.1%.

It can be seen from FIG. 8, the welded proportions of the area $A_i$ in the first direction 32 varies very much less than in the joining pattern according to FIG. 7. This is achieved with respect to the lowest possible index of variation of the ultrasonic welding points. In particular, it can be seen that a first partial joining pattern 60 that forms a part of a cuff base 28 and extends curved in the shape of an arc is formed from a set of several curves 62. The term curve is used here for a series of successive discrete ultrasonic welding points 30 (as can be seen in FIG. 5). This set of curves 62 is, for example, disposed in a range of approx. 200 to 270 mm, a small distance apart, and running parallel and largely in the first direction 32. In the adjoining area (of approx. 200 to approx. 50 mm), the curves 62 are curved in the shape of an arc, and the distance between increases in the first direction 32. In this way, it is inventively achieved that the area proportions $A_i$ of the 5 mm-sections in the first direction 32 do not vary as much, for example, as in the case of the joining pattern according to FIG. 7. In total, a very much lower index of variation of the area seized by the ultrasonic welding points results.

It is immediately apparent that there are several ways of ensuring that the variation of the area proportions $A_i$ of the 5-mm sections in the first direction 32 is not too large. A first possibility is to keep the radius of curvature of curved partial joining patterns as large as possible, that is, not to permit tight curvature. A further possibility, which is shown in FIG. 8, is the formation of curved partial joining patterns in the form of multiple curves or series of ultrasonic welding points, whose distance from each other is especially variable. Also, the distance between the individual ultrasonic welding points, in particular, those of a series could be varied. Also the area of the individual ultrasonic welding points or protrusions on the contour roller could be varied, in particular, additionally. Moreover, the disposition and the distance between the ultrasonic welding points in a second area, that is, where the ultrasonic welding points are further apart, can be varied.

Finally, FIG. 8 shows a second partial joining pattern 64 that is substantially straight and extends in the first direction 32. It is said to extend largely in the first direction 32 if, over a length of about 200 mm in the first direction 32, an extent in the second direction 34 of no more than 5 mm can be determined. A third partial joining pattern 66 is adjoined to this, which, like the first partial joining pattern 60, extends curved in the shape of an arc and comprises a set of several curves 62. It therefore also has a component in the second direction 34.

We claim:

1. A hygiene article, incontinence diaper or incontinence pad, the article having a longitudinal direction and a transverse direction perpendicular to the longitudinal direction as well as a central axis extending in the longitudinal direction, the article comprising:
   a nonwoven fabric or film component;
   at least one cuff element, with a nonwoven fabric component, on a left and right side of the hygiene article forming a left and right upstanding leakage barrier and extending substantially in the longitudinal direction of the article; and
   discrete ultrasonic welding points disposed in a joining pattern, said ultrasonic welding points disposed, structured and dimensioned to attach said cuff element to said nonwoven fabric or film component, wherein an extension of said joining pattern in the longitudinal direction exceeds an extension of said joining pattern in the transverse direction, said joining pattern having a central portion travelling substantially in the longitudinal direction of the article as well as rear and front end portions, said rear and front end portions curving inwardly towards the central axis of the article along an endwards directed extension of said joining pattern, wherein an index of variation of said joining pattern is no more than 40%, an area seized by said ultrasonic welding points having a density within said joining pattern which decreases in said rear and front end portions along said endwards directed and inwardly curved extension of said joining pattern.

2. The article of claim 1, wherein a separation between said welding points increases within said rear and front end portions along said endwards directed and inwardly curved extension of said joining pattern.

3. The article of claim 1, wherein an area seized by said ultrasonic welding points decreases within said rear and front end portions along said endwards directed and inwardly curved extension of said joining pattern.

4. The article of claim 1, wherein said joining pattern comprises a set of adjacent curves traveling at close proximity to another in said central portion and running parallel and largely in the longitudinal direction, said curves mapping into arc-shaped travel in said front and rear end portions, a distance between said curves thereby increasing within said rear and front end portions along said endwards directed and inwardly curved extension of said joining pattern.

5. The article of claim 1, wherein said index of variation of said joining pattern is no more than 35%.

6. The article of claim 1, wherein the article comprises a topsheet that is permeable at least in some areas, a backsheet that is impermeable at least in some areas, and a storage core that absorbs body fluids and is disposed between said top sheet and said back sheet.

7. The article of claim 6, wherein said nonwoven fabric or film component is said topsheet or said backsheet, wherein said cuff element is attached to said topsheet or said backsheet by said joining pattern.

8. The article of claim 1, wherein at least some areas of a first partial joining pattern constitute a cuff base.

9. The article of claim 8, wherein some areas of said cuff base are constituted by a second partial joining pattern that is substantially straight or largely parallel to the longitudinal direction.

10. The article of claim 9, wherein at least some sections of said cuff base are formed by said first partial joining pattern, said second partial joining pattern, and a third curved partial joining pattern.

11. The article of claim 10, wherein, in the longitudinal direction, said second partial joining pattern is disposed between said first and said third partial joining pattern.

12. The article of claim 1, wherein, in the longitudinal direction, said joining pattern has a first section, a center section and a third section adjoining said center section, wherein said first section, said center section and said third section have substantially equal lengths, said index of variation of said joining pattern in said first and/or said third section being no more than 40%.

13. The article of claim 1, wherein a distance between discrete said ultrasonic welding points in a first area is less than that in a second area.

14. The article of claim 13, wherein a distance between individual said ultrasonic welding points is 0.1 to 2.5 mm in said first area and 2 to 20 mm in said second area.

15. The article of claim 1, wherein a density per unit area of said ultrasonic welding points in a first area is greater than that in a second area.

16. The article of claim 13, wherein said first area forms at least one partial area of a first and/or second and/or third partial joining pattern of a cuff base.

17. The article of claim 13, wherein a first and/or third partial joining pattern comprises a set of at least two curves.

18. The article of claim 17, wherein at least two curves of said set are separated by a small maximum distance of 2 to 20 mm.

19. The article of claim 18, wherein at least two curves of said set are separated by a greater maximum distance of 10 to 70 mm.

20. The article of claim 17, wherein one or more of said curves has a radius of at least 60 mm.

21. The article of claim 17, wherein said curves have a variable distance between them.

22. The article of claim 1, wherein said joining pattern comprises first discrete ultrasonic welding points with an area of 0.3 to 4 $mm^2$.

23. The article of claim 1, wherein said joining pattern comprises first and second discrete ultrasonic welding points, an area of said first discrete ultrasonic welding points being smaller than that of said second discrete ultrasonic welding points.

24. The article of claim 1, wherein a sum of areas of said ultrasonic welding points of a 5-mm long section of said joining pattern in the longitudinal direction is on average 2 to 25 $mm^2$.

25. The article of claim 1, wherein a sum of areas of said ultrasonic welding points of a 5-mm long section of said joining pattern in the longitudinal direction is no more than 30 $mm^2$.

26. The article of claim 1, wherein a deviation of a sum of areas of said ultrasonic welding points of each 5-mm long section of said joining pattern in the longitudinal direction from a sum of areas of said ultrasonic welding points of a directly adjacent 5-mm long section of said joining pattern is less than 70%.

27. The article of claim 1, wherein a deviation of a sum of areas of said ultrasonic welding points of at least 50% of 5-mm long sections of said joining pattern from a sum of areas of said ultrasonic welding points of a directly adjacent 5-mm long section of said joining pattern is less than 40%.

28. The article of claim 1, wherein said joining pattern extends 300 to 2000 mm, in the longitudinal direction and 10 to 1200 mm in the transverse direction.

* * * * *